United States Patent
Pickart

(10) Patent No.: US 6,858,201 B2
(45) Date of Patent: Feb. 22, 2005

(54) METHODS FOR TREATING FINGERNAILS AND TOENAILS

(75) Inventor: Loren R. Pickart, Bellevue, WA (US)

(73) Assignee: Skin Biology, Inc., Bellevue, WA (US)

( * ) Notice: Subject to any disclaimer, the term of this patent is extended or adjusted under 35 U.S.C. 154(b) by 0 days.

(21) Appl. No.: 10/077,152

(22) Filed: Feb. 15, 2002

(65) Prior Publication Data

US 2003/0007938 A1 Jan. 9, 2003

Related U.S. Application Data

(60) Provisional application No. 60/269,603, filed on Feb. 15, 2001.

(51) Int. Cl.⁷ .................................................. A61K 7/04
(52) U.S. Cl. ........................ 424/61; 424/401; 514/887
(53) Field of Search ..................... 424/401, 451, 424/64

(56) References Cited

U.S. PATENT DOCUMENTS

| | | | |
|---|---|---|---|
| 4,186,188 A | * 1/1980 | Gumprecht | ............. 424/70.14 |
| 4,919,920 A | 4/1990 | Devos | |
| 5,382,431 A | * 1/1995 | Pickart | ...................... 424/401 |
| 5,484,586 A | 1/1996 | Bedard | |
| 5,554,375 A | 9/1996 | Pickart | |
| 5,660,818 A | 8/1997 | Dubief et al. | |
| 5,698,184 A | 12/1997 | Pickart | |
| 5,993,837 A | 11/1999 | Calello et al. | ............. 424/401 |
| 6,013,279 A | 1/2000 | Klett-Loch | |
| 6,331,569 B1 | 12/2001 | Kisters et al. | |

OTHER PUBLICATIONS

PCT Written Opinion, dated Mar. 24, 2003.

* cited by examiner

Primary Examiner—Thurman K. Page
Assistant Examiner—S. Howard
(74) Attorney, Agent, or Firm—Townsend and Townsend and Crew LLP

(57) ABSTRACT

Fingernail and toenail growth and repair are stimulated using an ionic metal-peptide complex. This also improves nail smoothness, strength and esthetic beauty. The peptide-ionic metal complex is comprised of an ionic metal selected from copper (II) or tin (II) and salts thereof, and the peptide component can be a acid, base, enzymatic, bacteria, or yeast hydrolyzate casein, collagen, elastin, meat products, silk protein, soybean protein, or other proteins or a chemically synthesized peptide that binds ionic metals, such as copper (II).

13 Claims, No Drawings

METHODS FOR TREATING FINGERNAILS AND TOENAILS

RELATED APPLICATION

This application claims priority to U.S. provisional patent application U.S. Ser. No. 60/269,603, filed Feb. 15, 2001.

BACKGROUND OF THE INVENTION

Beautiful, well-groomed fingernails are highly valued and, in an aesthetic sense, are the highlight of the hand and enhance a person's overall appearance. On a more utilitarian level, nails shield the ends of the fingers and toes from trauma and serve to protect the delicate sense of touch in the fingertips.

Nails are vestigial remnants of defensive weapons of our distant ancestors. In humans, nails evolved as aids for picking up small objects and for scratching. The nail is a direct outgrowth of the skin. The nails are primarily composed of keratin, the same hard tough protein that also forms the feathers and beaks of birds, the shells of turtles, lobsters, and crabs, the scales of fish, and the claws of animals.

Fingernails and toenails are living tissue. The nail is formed in a pocket of skin that has grown inward and is called the nail matrix. This area generates the nail and is also called the root of the nail. It appears wedge-shaped, with the nail plate fixed at the opening. The outer layer of the matrix contains specialized cells that create the keratin that grows out as the nail plate.

The nail plate is the commonly referred to as a person's fingernail or toenail. It is hard, smooth, shiny, somewhat rectangular, and slightly convex. The plate is translucent and essentially colorless, but appears pink because of the network of blood vessels under the nail bed below the nail plate. The nail plate grows as if in a 3-sided tunnel with no roof.

The nail bed is the finger tissue or toe tissue that supports the nail. The nail bed does not contribute to the outward growth of the nail but does supply necessary nutrients to the nail plate. The surface of the nail bed has vertical ridges and depressions that interlock into the nail plate to give a firm adhesion between the nail bed and the nail plate. The nail bed grows out along with the nail plate, and its elaborate network of blood capillaries help provide nutrition for the nail plate. When the nail plate is separated from the nail bed such as after an injury, the nail plate becomes discolored, cloudy and distorted.

Nails grow continuously throughout a person's life, growing approximately one-half to one millimeter weekly. For the nail plate to completely replace itself, from the time it is formed at the root until it reaches beyond the fingertip, takes from 5 to 7 months. Toenails grow much more slowly, about one-third to one-half the growth rate of fingernails.

In children, the rate of nail growth is high, and they have fingernails that are thick, strong, and smooth. But as individuals reach adulthood, this rate diminishes and nails become more fragile and possess a less smooth surface. Furthermore, injuries, stresses and the effects of human aging can weaken and thin nails, leading to premature breakage and tearing. Damage to the nails can also increase the incidence of fungal and bacterial infections of the nail bed and cuticles. Likewise, exposure of nails to harsh chemicals and alkaline conditions also weakens nail integrity. Nail polish removers also can cause nail damage. Such polish removers usually contain 98 percent to 100 percent acetonitrile or acetone, chemicals that can cause nail damage even after brief exposure. Another major source of nail damage is caused by the attachment of plastic artificial nails (cosmetic nails) over the true natural nail. The glues and adhesives used for attachment often severely weaken and thin the natural nail.

The treatment of fingernail and toe nail problems such as poor growth, lack of thickness and strength, lack of smoothness and tendencies to tear remains a major problem despite the development of numerous treatments such as the use of nail hardening polishes, protein elixirs such as bovine collagen emulsions, various types of wearable protective fingernail covers and so forth. The problem with current techniques for improving nail health is that they all are poorly effective, time consuming, and expensive when performed in nail salons.

SUMMARY OF THE INVENTION

The present invention provides, in one aspect, a method for stimulating the growth of nails in a mammal, including humans. A composition is administered to the nail bed and nail matrix that comprises an ionic metal-peptide complex in an amount effective to increase nail growth and thicken, strengthen and smooth the nail.

According to the invention, the peptide-ionic metal complex is comprised of an ionic metal selected from the group consisting of copper (II) and tin (II) and therapeutically acceptable salts and complexes thereof. The peptide component of the complex can be a hydrolysis of casein, collagen, elastin, meat products, silk protein, or soybean protein, such as hydrolysis formed enzymatically, with acid, base, bacteria, or the like. The peptides mixtures secreted by cultures of yeast or bacteria can also be used. The peptides can also be prepared by chemical synthesis. Typically, the composition will be administered topically, and the concentration of the ionic metal-peptide complex in the composition, although it can vary widely depending on the particular use, is typically about 1% to about 25%.

DETAILED DESCRIPTION OF THE SPECIFIC EMBODIMENTS

Treatment methods and compositions are provided to enhance nail growth and improve nail health, thickness, strength, smoothness and beauty, using metal ions complexed with peptides to facilitate and speed the process of nail regeneration.

The methods comprise administering to nail matrix and nail bed a therapeutically effective amount of a composition, which comprises the peptide-metal complex described herein in an amount, and for a length of time, sufficient to enhance nail regeneration.

As used herein it will be understood that "peptide" refers to synthetically and biologically produced peptides, as well as to peptone mixtures, which are obtained by the hydrolysis of larger peptides, polypeptides and proteins.

Peptones are generally comprised of intermediate polypeptide products and mixtures of small peptides, formed in partial hydrolysis of proteins. Among the types of protein digests useful in the invention are digests of soybean protein, casein, collagen, elastin, meat products (e.g., PRIMATONE), such as beef, liver, silk protein and so forth. By peptone digest is meant that the protein is degraded by enzymatic digestion or by acid or base hydrolysis, or by the bacterial cultures that internally hydrolyze proteins and secrete the subsequent peptides, oR by bacterial cultures that secrete hydrolytic enzymes in a culture medium which then hydrolyze proteins in the culture medium, according to well known procedures, such as described in Remington's Pharmaceutical Sciences, Mack Publishing Co., Easton, Pa. pp. 428–429 (1975), which is incorporated herein by reference, using enzymes such as papain, etc. Many peptone digests are widely available commercially, such as from Sigma Chemical Company, St. Louis, Mo.

The synthetic peptide Gly-His-Lys as well as many others, are available from commercial sources, such as BaChem of Basel, Switzerland.

Metal Salts

Ionic metal complexes of copper and tin are widely available commercially, such as from Sigma Chemical Company, St. Louis, Mo.

Formation of Metal Organic Complexes

A peptide is combined with an amount of an aqueous solution of ionic metal salt sufficient to form a complex. The process is described in U.S. Pat. Nos. 5,382,431, 5,554,375, and 5,698,184, the disclosures of each being expressly incorporated herein by reference.

Typically, the complex is then combined with a pharmaceutically acceptable carrier to form a cream, lotion, or solution in a concentration of from about 0.1% to about 25% peptide-metal complex or more. The preparation may be sterilized or pasteurized, as desired, without destroying the activity of the peptide-metal complex.

To produce the complexes useful in the present invention, the peptides are complexed with one or more ionic metals, such as copper, tin, or the salts thereof, such as sulfate, acetate, phosphate, etc., as described above. In one method for preparing the organic-metal complex, the peptide is dissolved in warm water (about 40° C. to 60° C.) at a concentration of about 20 to 50% (weight/volume), and then mixed with an aqueous solution of a metal salt complex at a salt concentration of about 10 to 50% (w/v). If desired, isolation and purification of the peptone-copper complexes can then be accomplished by any suitable separation or purification procedure such as, for example, filtration, extraction, centrifugation, crystallization, or a combination of these procedures.

By complexed is meant that the peptides and metal ions form electrostatic bonds, although this mechanism is offered by way of possible explanation only and not by way of limitation.

The pH of the mixture is adjusted (with sodium hydroxide or the like) to a pH between 5.0 and 7.0, and other aqueous components, as desired, are added, followed by blending in of carriers, smootheners, etc., for preparing a final formulation.

The peptide-metal complexes of the invention may be administered for a variety of therapeutic, prophylactic or cosmetic uses as described herein to humans or in veterinary applications to other warm-blooded mammals. Among veterinary animals particularly well suited for treatment with the present compositions are species of hooved mammals (ungulates) such as equine, bovine, porcine, ovine, caprine, and animals having claws or nails (unguiculates) such as canine, avian, feline, primates, etc. Show animals suffering from or susceptible to hoof or nail damage and disease scarring are particularly well suited for treatment according to the present invention.

The compositions and pharmaceutical preparations thereof are intended for local, topical, oral or parenteral (e.g., subcutaneous injection) administration for prophylactic and/or therapeutic or a cosmetic treatment regimen, to facilitate nail remodeling and regeneration. Preferably, the compositions, including pharmaceutical compositions, are administered locally, e.g., topically, as a paste, cream, ointment, salve, lotion, gel, spray, etc., separately or in conjunction with a wound dressing, bandage, and the like.

For administration to warm-blooded animals, the peptide-metal compositions will typically be sterilized and incorporated in pharmaceutical or veterinary formulations. If desired, such compositions can be sterilized using conventional, well-known sterilization techniques, e.g., boiling or pasteurization, without substantially adversely affecting the biological activity of the peptide-metal complexes. The compositions may contain pharmaceutically acceptable auxiliary substances as may be required to approximate physiological conditions and as may be desirable to prepare compositions for convenient administration, such a pH adjusting and buffering agents, and delivery vehicles.

Actual methods for preparing pharmaceutically administrable compounds will be known or apparent to those skilled in the art and are described in detail in, for example, Remington's Pharmaceutical Science, supra.

Depending on the intended mode of administration and the intended use, the compositions may be in solid, semi-solid, or liquid dosage forms, such as, for example, powders, granules, crystals, liquids, suspensions, liposomes, pastes, creams, salves, etc., and may be in unit-dosage forms suitable for administration of relatively precise dosages. The compositions may include a conventional pharmaceutical carrier or excipient and, in addition, may include other medicinal agents, growth factors, wound sealants, carriers, etc., as further described below.

For semi-solid compositions, as would be appropriate for pastes and creams intended for topical administration, the peptide-metal complexes can be provided separately or may be compounded with conventional nontoxic carriers such as, for example, aloe vera gel, squalene, glycerol stearate, polyethylene glycol, cetyl alcohol, stearic acid, and propylene glycol, among others. Such compositions may contain about 1–50% active ingredient, more preferably about 1–25%. Thus, the final concentration of copper or other metal in a formulation can range from about 0.1 or 0.15% (w/v) up to 0.4 to 0.8% or 1.6%, and in some instances up to 2 to 5% or more, although it will typically be desirable to employ the lowest final concentration of copper or other metal as possible which achieves the desired therapeutic or cosmetic effect.

The concentration of the peptide-metal complexes in these formulations can vary widely, and will be selected primarily by intended use, viscosities, etc., in accordance with the those skilled in this art; for example, see Remington's Pharmaceutical Science, 17th ed., Mack Publishing Company, Easton, Pa. (1985), which is incorporated herein by reference. The composition or formulation to be administered will, in any event, contain a quantity of the peptide-metal complexes sufficient to achieve the desired effect in the subject being treated.

The compositions of the invention are administered to a warm-blooded animal, such as humans, already suffering from an inadequate nail growth and poor nail health. Amounts adequate to accomplish these effects are defined as a "therapeutically effective doses." Amounts effective for this use will depend on the severity of the nail condition but generally range from about 0.01 mg to about 50 mg per day of peptide-metal complex per day per square centimeter of the nail site, with dosages of from about 1 mg to 25 mg, sometimes about 3, 5 or 10 mg up to about 15 or 20 mg per day per square centimeter of the nail site being more commonly used. Maintenance dosages over a prolonged period of time, e.g., daily administration for weeks to months, may be adjusted as necessary.

For veterinary uses higher levels may be administered as necessary. Determining actual amounts of the peptide-metal complexes necessary to treat a particular condition as described herein will be through standard empirical methods well known in the veterinary art. A representative lotion formulation for application to the nail comprises, in approximate amounts (expressed as final concentrations, w/v %): water, 62.9; cetyl alcohol, 5.0; stearic acid, 5.0; ARLACEL 165, 7.0; LEXOL EHP, 4.0; squalene, 5.0; copper chloride-$2H_2O$, 0.40; soybean peptone, 6.0; mineral oil, 3.0; allantoin, 0.5; GERMABEN-II-E, 1.0; herbal fragrance, 0.1; aloe vera powder, 0.1; vitamin A–D, 0.01; vitamin E, 0.01.

The peptide-metal complexes of the invention may be administered in relatively large amounts without serious side effects.

The following examples are offered by way of illustration, not by way of limitation.

EXAMPLE I
Preparation of Active Peptone-metal Complexes

This Example describes methods used in the preparation of the peptone-metal complexes having biological activities described further below. In general, the preparation of peptone-metal complexes is described in U.S. Pat. Nos. 5,382,431, 5,554,375 and 5,698,184, incorporated herein by reference. Soybean peptone was obtained from Sigma Chemical Company, St. Louis, Mo. (type IV, number P 0521), as was cupric chloride hydrate (no. C 6641) and tin (II) chloride, 99% pure.

Soybean peptones (enzymatic digests of soybean protein) were dissolved in warm water (40° C.) at a concentration of 20% (weight/volume), and then mixed with an aqueous solution of a metal salt (copper (II) chloride or tin (II) chloride) at a salt concentration of 20% (w/v). The pH of each soybean peptide-metal complex mixture is adjusted with sodium hydroxide to a pH value between 6.0 and 7.0. The resulting precipitate containing the peptide-metal complexes is removed by centrifugation at 10,000×G for 20 minutes, then processed as a wet paste into further products, e.g., the sticky paste can be applied directly to the skin or more usually is formulated to a desired final concentration into creams, lotions, sprays, etc.

Other types of enzymatic protein digests such as those of casein, collagen, elastin, meat products, silk protein and the like, and other metal salts of the metals, such as sulfate, acetate, phosphate and so forth will work similarly.

EXAMPLE II
Preparation of Active Peptide-metal Complexes

The synthetic peptide Gly-His-Lys was purchased from a commercial source (Sigma Chemical Company, St. Louis, Mo.) and is available from other custom manufacturers.

Peptides were dissolved in warm water (40° C.) at a concentration of 20% (weight/volume), and then mixed with an aqueous solution of a metal salt (copper (II) chloride) at a salt concentration of 20% (w/v), as described above.

EXAMPLE III
Improvement in Fingernail Growth in Humans by Using Copper Complexes This Example describes the use of a cream prepared with the complexes of peptone with copper (II) to improve nail growth in humans. The copper soy peptone complex (0.3% copper ion and 4% dry weight of peptone) was mixed into an application cream containing 55% (by weight) aloe vera gel, 12% squalane, 12% glycerol stearate, 5% PEG-100, 4% cetyl alcohol and 0.3% retinol. The placebo-treated control nails were treated with a similar cream that contained no copper-peptide complex.

For testing experiments, the fingernail growth rates of the index finger were used as a measurement. In the first set of experiments, the copper-peptide complex was applied to the index fingernail and cuticle on the right hand while the left hand nail was untreated and used as a control. In the second set of experiments with different human volunteers, the copper-peptide cream was applied to the index fingernail and cuticle on the left hand while the right hand nail was treated with the placebo cream and used as a control.

Nails were treated daily for four weeks. Nail length was measured from the end of the nail bed to the tip of the nail at its center by pushing a small plastic ruler under the nail and firmly against the nail bed. The nails were also visually inspected to determine that the treated nails appeared to be longer on the treated band and this was readily apparent in all cases. The effect of nail growth stimulation was approximately similar if either the right hand treated group or the left hand treated group was used.

As seen in Table 1, nails treated with the copper-peptide complex had better nail growth.

TABLE 1

First Experiment

| | | Finger Nail Growth (Millimeters in four weeks) | |
|---|---|---|---|
| | Sex | Right Hand Treated | Left Hand (Placebo Control) |
| Person 1 | M | 4.2 | 2.7 |
| Person 2 | M | 3.2 | 2.1 |
| Person 3 | F | 4.3 | 3.2 |
| Person 4 | F | 3.8 | 2.9 |
| Person 5 | F | 3.9 | 2.6 |

Second Experiment

| | | Finger Nail Growth (Millimeters in four weeks) | |
|---|---|---|---|
| | Sex | Left Hand Treated | Right Hand Untreated Control) |
| Person 6 | M | 2.8 | 1.5 |
| Person 7 | M | 3.7 | 2.6 |
| Person 8 | F | 4.1 | 3.0 |
| Person 9 | F | 4.1 | 2.6 |
| Person 10 | F | 3.5 | 2.2 |

EXAMPLE IV
Improvement in Fingernail Growth in Humans by Using Tin (II) Peptone Complex.

This Example describes the use of a cream prepared with the complexes of peptone with tin (II) to improve nail growth in humans.

For testing experiments, the fingernail growth rates of the index finger were used as a measurement. In the experiments, the copper-peptide complex was applied to the index fingernail and cuticle on the right hand while the left hand nail was treated with the placebo cream and used as a control.

Nails were treated daily for four weeks. Nail length was measured from the end of the nail bed to the tip of the nail at its center by pushing a small plastic ruler under the nail and firmly against the nail bed. The nails were also visually inspected to determine that the treated nails appeared to be longer on the treated hand, and this was readily apparent in all cases.

As seen in Table 2, Nails treated with the tin-peptide complex had better nail growth.

TABLE 2

| | Sex | Finger Nail Growth (Millimeters in four weeks) | |
| --- | --- | --- | --- |
| | | Right Hand Treated | Left Hand Placebo Control |
| Person 1 | M | 4.8 | 3.5 |
| Person 2 | M | 3.6 | 3.3 |
| Person 3 | F | 3.1 | 1.2 |
| Person 4 | F | 2.9 | 1.9 |
| Person 5 | F | 4.4 | 2.5 |

EXAMPLE V

Improvement in Fingernail Growth in Humans by Using GHK-copper (II)

This Example describes the use of a cream prepared with the complexes of GHK-Copper (II) to improve nail growth in humans.

For testing experiments, the fingernail growth rates of the index finger were used as a measurement. In the experiments, the copper-peptide complex was applied to the index fingernail and cuticle on the right hand while the left hand nail was treated with a placebo cream and used as a control.

Nails were treated for four weeks. Nail length was measured from the end of the nail bed to the tip of the nail at its center by pushing a small plastic ruler under the nail and firmly against the nail bed. The nails were also visually inspected to determine that the treated nails appeared to be longer on the treated hand, and this was readily apparent in all cases.

As seen in Table 3, nails treated with the GHK-Copper complex had better nail growth.

TABLE 3

| | Sex | Finger Nail Growth (millimeters in four weeks) | |
| --- | --- | --- | --- |
| | | Right Hand Treated | Left Hand Placebo Control |
| Person 1 | M | 3.7 | 2.8 |
| Person 2 | M | 3.4 | 1.9 |
| Person 3 | F | 2.9 | 2.4 |
| Person 4 | F | 3.1 | 2.3 |
| Person 5 | F | 3.5 | 2.6 |

EXAMPLE VI

Reduction in Nail Tearing

A woman 67 years old had chronic problems with her nails tearing and ripping. She used the copper-peptide cream for three months and was observed to have no fingernail tears after 3 weeks of application of the cream. She remarked that her nails looked healthier and more beautiful.

EXAMPLE VII

Smoothing of Nails

A woman 55 years old had nails with a rough and "bumpy" surface. She used the copper-peptide cream for three months and observed a smoothing of her nails, and a more beautiful appearance.

EXAMPLE VIII

Healthier Toenails

A woman 81 years old with complications of diabetes had difficulty cutting her toenails without tears and rips developing. She used the copper-peptide cream for three months and was observed to have toenails that cut evenly without rips or tears.

EXAMPLE IX

Healthier Toenails

A woman 41 years old had chronic problems with nails tearing after removing cosmetic (plastic nails). By using the copper peptide cream, she found her nails became hard and strong much faster after the removal of the cosmetic nails.

EXAMPLE X

Healthier Fingernail

A man of 54 years had chronic problems with fragile fingernails due to working in a position that required hand-washing numerous times daily. He applied the copper-peptone cream nightly to his nails for three months and was observed to have a cessation of nail problems.

EXAMPLE XI

Healthier Fingernail

A woman 30 years old had chronic problems with uneven and fragile fingernails due to working in a position that required hand washing numerous times daily. She applied the copper-peptone cream nightly to her nails for three months and was observed to develop smoother nails that were hard and strong.

EXAMPLE XII

Animal Treatment

A five year old horse had a badly cracked hoof. A copper-peptide cream was rubbed into the cracked area three times a week for three months. At the end of this time the cracks had healed and the outer surface of the hoof look much smoother and healthier.

EXAMPLE XIII

Animal Treatment

A three year old horse had many small cracks and damage on the hoof. A copper peptide cream was rubbed into the cracks and over the hoof surface for three times a week for three months. At the end of this time, most of the cracks had healed and the outer surface of the hoof looked much smoother and healthier.

Although the foregoing invention has been described in some detail by way of illustration and example for purposes of clarity of understanding, it will be obvious that certain changes and modifications may be practiced within the scope of the appended claims.

What is claimed is:

1. A method for stimulating the growth of fingernails, toenails, or hooves in a mammal, comprising administering to the nail or hoof a composition that comprises a ionic metal-peptide complex in an amount effective to stimulate nail or hoof growth.

2. The method of claim 1, wherein the ionic metal is selected from the group consisting of copper (II) or tin (II) and therapeutically acceptable salts and complexes thereof, wherein the concentration of the ionic metal-peptide complex in the composition is 1% to 25%.

3. The method of claim 1, wherein the ionic metal is copper (II).

4. The method according to claim 1, wherein the peptide of the ionic metal-peptide complex is an enzymatic hydrolysis of casein, collagen, elastin, meat products, silk protein, or soybean protein.

5. The method according to claim 1, wherein the peptide of the ionic metal-peptide complex is an acid hydrolysis of casein, collagen, elastin, meat products, silk protein, or soybean protein.

6. The method according to claim 1, wherein the peptide of the ionic metal-peptide complex is a basic hydrolysis of casein, collagen, elastin, meat products, silk protein, or soybean protein.

7. The method according to claim 1, wherein the peptide of the ionic metal-peptide complex is a bacterial hydrolysis of casein, collagen, elastin, meat products, silk protein, or soybean protein.

8. The method according to claim 1, wherein the peptide of the ionic metal-peptide complex is a chemically synthesized copper binding peptide.

9. The method according to claim 1, wherein the peptide of the ionic metal-peptide complex is a chemically synthesized peptide and the ionic metal is copper (II), or tin (II).

10. The method according to claim 1, wherein the ionic metal-peptide complex is combined with a carrier to form a cream or lotion.

11. The method according to claim 1, wherein the concentration of the ionic metal-peptide complex in the composition is 1% to 25%.

12. A method for improving nail and hoof health, smoothness, and strength in a mammal, comprising administering to the nail or hoof of said mammal a pharmaceutical composition that comprises a ionic metal-peptide complex in an amount effective to stimulate growth and repair and smooth and strengthen the nail or hoof of said mammal.

13. A method for stimulating the growth and repair of a damaged fingernail, toenail, or hoof of a mammal, comprising:

administering to the damaged fingernail, toenail or hoof a composition that comprises a ionic metal-peptide complex in an amount effective to stimulate growth and repair of the damaged fingernail, toenail or hoof.

* * * * *